(12) United States Patent
Barbosa et al.

(10) Patent No.: US 9,696,280 B2
(45) Date of Patent: Jul. 4, 2017

(54) DEVICE AND METHOD FOR INSPECTING ALUMINUM CABLES WITH A STEEL CORE (ALUMINUM CONDUCTOR STEEL REINFORCED—ASCR) INSTALLED IN ENERGIZED ELECTRICAL ENERGY LINES

(71) Applicants: Light Serviços de Eletricidade S/A, Rio de Janeiro (BR); Fundação CPQD—Centro de Pesquisa e Desenvolvimento em Telecomunicações, Campinas (BR)

(72) Inventors: Célio Fonseca Barbosa, Campinas (BR); Flávio Eduardo Nallin, Campinas (BR); Raphael Nunes de Souza, Campinas (BR)

(73) Assignees: Light Serviços de Electricidade S/A, Rio de Janeiro (BR); Fundação CPQD—Centro de Pesquisa e Desenvovlvimento em Telecomunicações, Campinas (BR)

( * ) Notice: Subject to any disclaimer, the term of this patent is extended or adjusted under 35 U.S.C. 154(b) by 179 days.

(21) Appl. No.: 14/796,684

(22) Filed: Jul. 10, 2015

(65) Prior Publication Data

US 2017/0010240 A1  Jan. 12, 2017

(51) Int. Cl.
*G01N 27/82* (2006.01)
*G01N 27/90* (2006.01)
*G01N 27/87* (2006.01)

(52) U.S. Cl.
CPC ......... *G01N 27/9006* (2013.01); *G01N 27/82* (2013.01); *G01N 27/87* (2013.01); *G01N 27/902* (2013.01); *G01N 27/9013* (2013.01); *G01N 27/9033* (2013.01); *G01N 27/9046* (2013.01)

(58) Field of Classification Search
CPC .... G01N 27/82; G01N 27/87; G01N 27/9013; G01N 27/902; G01N 27/9033; G01N 27/9046
USPC ... 324/51, 55, 200, 228, 234, 236, 237, 244, 324/260, 300, 323, 332
See application file for complete search history.

(56) References Cited

U.S. PATENT DOCUMENTS

| 4,652,823 | A | * | 3/1987 | Sutton | G01N 27/9046 324/233 |
| 5,744,955 | A | * | 4/1998 | Booker | G01N 27/9013 324/228 |
| 2007/0291438 | A1 | * | 12/2007 | Ahrens | F16K 31/06 361/160 |

* cited by examiner

*Primary Examiner* — Jermele M Hollington
*Assistant Examiner* — Raul Rios Russo
(74) *Attorney, Agent, or Firm* — Michael Best & Friedrich LLP

(57) ABSTRACT

This invention concerns a device and a method for inspecting aluminum cables with a steel core (ASCRs), installed in energized electrical energy lines, which use the ECT (Eddy Current Testing) technique for evaluating the remaining thickness of the zinc layer which covers the steel wires of the cables inspected, where the readings of the tension of the detection solenoid and the current of the excitation solenoid are taken as the current of the conductor reaches zero, the electrical parameters of the conductor are corrected for the average temperature during the inspection and the signal from the detection solenoid is filtered through a hybrid circuit which is designed to increase the sensitivity of the measurement.

5 Claims, 3 Drawing Sheets

DEVICE AND METHOD FOR INSPECTING ALUMINUM CABLES WITH A STEEL CORE (ALUMINUM CONDUCTOR STEEL REINFORCED—ASCR) INSTALLED IN ENERGIZED ELECTRICAL ENERGY LINES

FIELD OF APPLICATION

This invention, in a general sense, concerns the inspection of cables of electrical energy distribution and transmission networks, in particular, the inspection of aluminum cables with a steel core, installed in energized electrical energy lines.

BASIS FOR THE INVENTION

Electrical energy lines are normally formed of conductor cables of the ASCR type (Aluminum conductor steel reinforced), which are composed of a nucleus of galvanized steel wires covered by one or two layers of aluminum wires. The steel nucleus provides mechanical support for the cable, while the aluminum wires conduct the electrical current. With the passing of the years and exposure to weathering, the steel nucleus suffers a process of corrosion which progressively consumes the zinc layer which constitutes the galvanization of the nucleus. Once the zinc is consumed, the contact between the aluminum and steel gives rise to a process of accelerated corrosion (galvanic corrosion) which degrades the mechanical properties of the steel and leads to breakage of the cable. Depending on the line and the section where the cable suffered the breakage, the consequences may be grave, such as a loss of energy for a large section of the population and/or accidents involving vehicles and people, if the cable falls on a highway or an inhabited area.

As the steel nucleus is covered by aluminum wires, the corrosive process cannot be detected by visual inspection. As such, the concessionaire is restricted to the criterion of replacing the conductor based on its date of installation. This criterion frequently leads to the replacement of conductors in good condition, as they were installed in a less hostile environment. Moreover, the criterion of the date of installation also results in the risk of leaving conductors in service which are already compromised, as they were installed in a more hostile environment. Thus, there is a need for a device which carries out the inspection of a conductor installed in a transmission line and provides an indication of its state of repair.

An initial device was developed by the authors of this invention, whose principal innovating aspects were claimed through a patent application filed with the BPO on Aug. 6, 2007 [1]. However, the cited device only operates with de-energized electrical lines, which represents a limitation on its use, as it requires the planning of work involving different agents, due to the need to disconnect the line which is to be inspected. Depending on the line, it cannot simply be disconnected and, even when it can, it may be necessary to request prior authorization from the ONS (National System Operator). In addition to this, in cases where the line may be disconnected, the time when it may remain in this condition is relatively short, which restricts the number of sections which can be inspected. Thus, the possibility of using the inspection device with the line energized significantly increases its potential application by the electrical energy concessionaires, which prompted the development of the invention described in this document.

OBJECT OF THE INVENTION

This invention concerns a device and a method for inspecting aluminum cables with a steel core (ASCRs) installed in energized electrical energy lines, which use the ECT (Eddy Current Testing) technique to evaluate the remaining thickness of the layer of zinc which covers the steel wires of the inspected cables.

DESCRIPTION OF THE STATE OF THE ART

Figure 1:
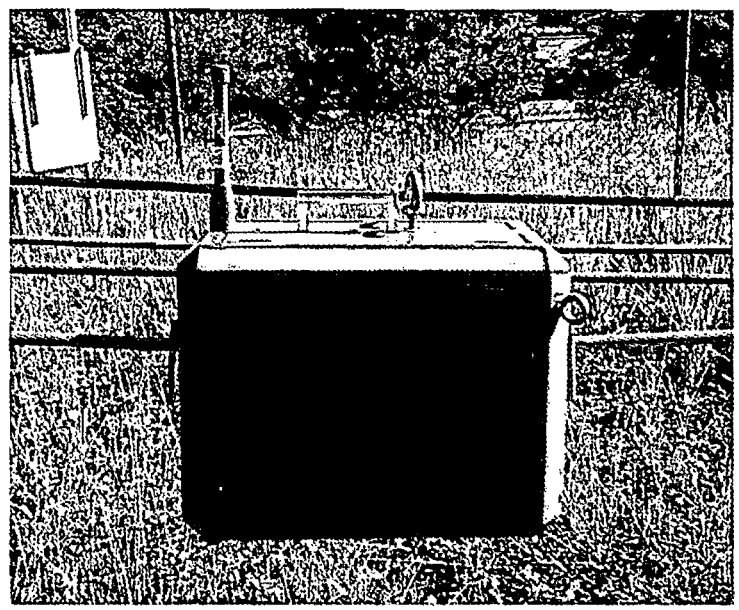
FIG. 1 is a photograph of the robot used to inspect the energized line in which the device of this invention is installed.

There are some devices on the market for the inspection of the nucleus of ASCR cables installed in electrical energy transmission lines. The most commonly used technique was developed at the start of the 20th century for the inspection of steel cables used in underground mining, known as WRT (Wire Rope Test) [2]. In its most common implementation, this technique uses a stationary magnetic field source (usually a strong permanent magnet) to magnetize the nucleus of the steel cable. A series of magnetic field sensors is installed in the vicinity of the steel cable to capture the variations in the "signature" of the magnetic field in its surroundings. These sensors were originally implemented in the form of small bobbins and are currently used by Hall effect transducers. These variations are associated with localized defects (for example, severed or dented wires) in the steel cable, which are referred to in the technical literature as LF (Local Fault). It is common for some WRT magnetic field sensors to be installed together with the permanent magnet, in order to pick up a signal proportional to the full flow of the magnetic circuit formed by the permanent magnet and the steel cable. This flow is affected by the area of steel present in the cable, and may be adjusted to provide a reading of the loss of area, which is known as the LMA (Loss of Metallic Area). The WRT is widely disseminated, there being several patents exploring specific aspects not covered by the previous patents. [3]-[7]

The use of WRT for inspecting ASCR conductors in electrical energy transmission lines was originally achieved with equipment developed for inspecting steel cables and adapted for use in ASCR cables. For example, Intron (Russia) has experience in the use of its equipment in electrical energy lines, one of the devices being described in the patent US RE 40166E [8]. In an application made by Intron, the equipment is transported manually by the operator, for which purpose he has to mount the conductor and cross the section of the line with the instrument. Progress in this application was achieved by Kinetrics (Canada) [9], where the measuring device is transported along the line using a remote-controlled robot. The Kinetrics device was initially developed to operate on de-energized lines, having recently evolved to work on energized lines. This device is known by the registered mark LineVue. Cepel (Brasil) [10]-[11] has also developed a remotely-operated system, based on WRT, for use on energized lines. An interesting variation of the WRT technique applied to ASCR conductors is described in Patent EP 1000349A1 [12], which uses a gyratory magnet to magnetize a steel nucleus.

An alternative technique which may be used in the inspection of steel conductors is based on the induction of Eddy Currents in steel [wires], which is known as Eddy Current Testing. This technique is also old, having been theoretically addressed by Forster and Stambke [13] in 1954. A detailed and more rigorous theoretical approach to this technique was adopted by Wait and Gardner [14]. In general terms, ECT consists of using a solenoid to generate an alternate magnet field along the conductor and another to detect the resulting magnetic flow. This resulting magnetic flow is sensitive to the electrical properties of the conductor, which allows for an evaluation of the thickness of the galvanization layer over the steel wires. The use of ECT for inspecting conductors installed in electrical energy transmission lines was achieved for the first time by the National Grid (United Kingdom) [15], which subsequently licensed the technology for use by Cormon [16], now Cormon-Teledyne. In this development, the ECT device is moved along the conductor of a de-energized line by a remotely controlled robot. A similar device was developed by the Tokyo Electric Power Company (Japan) in conjunction with Fujikura [17] for the inspection of disconnected lines.

Attempts to use ECT on energized lines apparently have not been successful up to the present. In fact, migration from the Cormon system to energized lines was achieved by Ontario Hydro (Canada) [18] and, as a result of the difficulties encountered, Ontario Hydro Research (now Kinectrics) replaced ECT with WRT in its inspection system (LineVue). Recently, a research report by the National Grid (United Kingdom) informed that technical cooperation has been established with Hydro Quebec (Canada) to develop an ECT sensor for inspecting ASCR conductors in energized lines [19].

Limitations of the Existing Products on the Market

As may be seen in the previous section, the existing products on the market mainly use WRT (Wire Rope Test), with ECT (Eddy Current Test) being restricted to de-energized lines. As such, the advantages and disadvantages of the existing products are associated with the characteristics of these technologies.

For use on electrical energy lines, WRT presents the advantage of being highly insensitive to the current which circulates through the conductor which is being inspected. This characteristic enables the use of WRT on energized lines, requiring few adaptations in relation to the device which operates on energized lines. On the other hand, WRT presents some disadvantages for the inspection of ASCR conductors, the principal such being described below.

a) One disadvantage of the WRT technique concerns the subjectivity of the LF (Local Fault) reading as this involves a qualitative evaluation of the signal received and not the measurement of a well-defined physical magnitude. Normally, in applications which involve steel cables, a suspicious signal from an LF reader requires a visual evaluation of the cable to determine if there really is a defect. In other words, the LF signal serves as an alarm to indicate that there may be a fault at that point of the cable, requiring an inspector to physically check the integrity of the cable at that point. Although it is effective for steel cables, this procedure does not apply to ASCR cables, as the steel wires are covered by the aluminum wires.

b) The reading of the LMA (Loss of Metallic Area) also presents a disadvantage in application to ASCR cables, as it can only detect a process of corrosion after this has reduced the mass of steel in a considerable section of the cable. This means that the corrosive process is in full development, and may compromise the structural integrity of the cable in a short space of time. For inspection of steel cables this characteristic is not critical, as the test may be repeated frequently, with a view to monitoring the development of the corrosion and determining the time to replace the cable. Indeed, some applications of WRT in steel cables in mines use continuous monitoring of the LMA reading, in order that their development is followed in real time. Whereas, in the case of electrical energy lines, due to the operational aspects and costs involved in an inspection, it is rarely justifiable to carry out measurements on the same section of a line at short time intervals. Strictly speaking, if a process of advanced corrosion is detected in a section of the line, it makes more sense for the concessionaire to replace this section than to carry out periodic inspections over a short space of time.

c) The LMA reading represents an estimate of the average area of metallic material in the section covered by the sensor (typically 30 to 50 cm). So, for the LMA reading to be consistent, the reduction in the area should be relatively uniform along the section covered by the sensor. Otherwise, the LMA reading will indicate that the cable is in a better state that it really is.

d) Another aspect to consider in the use of the WRT technique in the inspection of ASCR cables is that, unlike steel cables, in ASCR cables the oxides produced by corrosion remain contained in the steel nucleus due to the pressure of the aluminum layers. As a consequence, the reading of the LMA sensor will indicate a remaining metallic area greater than that which is actually in the cable.

e) The presence of layers of aluminum wires over the steel wires is also a problem for the use of WRT in ASCR cables, as it reduces the sensitivity of the LF and LMA readings for an ASCR cable, when compared with the readings of a steel cable.

Having described the problems and deficiencies of the use of the WRT technique in ASCR cables, it remains to undertake the same analysis for the ECT technique. It is emphasized that the main advantage of the ECT technique is that it allows a quantitative reading of the characteristics of the cable and, in particular, the thickness of the galvanization layer present in the steel wires, which allows for the detection and monitoring of the corrosive process even in its initial stages. The main disadvantages are:

a) The ECT technique is susceptible to the presence of current in the conductor being monitored which, in principle, limits its use exclusively to de-energized lines.

b) The ECT reading is also sensitive to the temperature of the conductor, which renders it more problematic on energized lines.

c) The presence of layers of aluminum wires over the steel wires is also a problem in the use of ECT in ASCR cables, as it reduces the sensitivity of readings carried out for an ASCR cable, when compared with the readings of a steel cable.

Causes of the Limitations of the Existing Products on the Market

Devices which Use WRT

The causes of the problems associated with the devices which use WRT (Wire Rope Test) on ASCR cables are described below.

a) The LF (Local Fault) is intrinsically subjective, as it is associated with disturbances in magnetic field lines caused by alterations in the structure of the cable. Imagine, for example, a magnetized steel cable which is perfectly uniform and moves at constant speed. A magnetic field sensor positioned on this cable will sense a uniform magnetic field. If an alteration is introduced into this cable (for example, by a severed wire), the lines of the magnetic field will alter its configuration in the vicinity of the point of rupture of the wire. On passing by the sensor, the latter will sense this alteration and the signal will present a small impulse. This signal serves only as an indication that something different has happened on the section of cable, but it is not possible to know what. In inspections of steel cables, if the signal of the disturbance is reasonably strong, the operator will schedule a cable stoppage to inspect the point. However, with ASCR cables, this is not possible, as even if the robot which carries the WRT sensor has a video camera, the aluminum wires do not allow the steel nucleus to be inspected visually.

b) The LMA (Loss of Metallic Area) reading is obtained from the resistance of the magnetic circuit formed by the permanent magnet, the non-magnetic intervals (air and aluminum) between the magnet and the nucleus, and the steel nucleus. The resistance of the steel nucleus is proportional to its length and inversely proportional to the area of its straight section. As such, a reduction in the area of the straight section of the nucleus results in an increase in the resistance of the magnetic circuit which, in turn, is sensed by the sensor as a reduction of the magnetic field. For the LMA reader to be reliable, it is necessary for a reasonable mass of steel to have been removed, which means that the corrosive process is already in full swing. In the case of ASCR cables, the corrosive process is accelerated by contact between two different metals (galvanic corrosion), which can compromise the structural integrity of the cable in a short space of time. Thus, this characteristic of the LMA reader does not contribute to its use in the inspection of ASCR cables.

c) To understand why the LMA reader tends to underestimate the loss of metallic area in short sections, let us consider a section of cable which presents a loss of area of 50% concentrated in only 10 cm. In this case, the LMA reading of a sensor of 50 cm will be 17%, which is to say, it will indicate that the cable still has 83% of its original area. Thus, as the rupture load of the cable is proportional to its minimum area of straight section, the LMA reading will indicate that the cable retains 83% of its original capacity, while, in fact, it retains only 50%.

d) As different kinds of ferrous oxides present ferromagnetic properties, the result of corrosion retained over the steel nucleus will be seen as a metallic area by the LMA sensor. As a consequence, the LMA reading will indicate a larger metallic area than there really is.

e) The presence of aluminum wires reduces the sensitivity of the WRT technique by increasing the section without magnetic material between the magnet and the steel nucleus. This section without magnetic material presents high magnetic resistance, which reduces the total magnetic flow.

Devices which Use ECT

The causes of the problems associated with the devices which use ECT (Eddy Current Test) on ASCR cable lines are described below.

a) The ECT technique depends on the magnetic permeability of the steel, which is to say, the signal obtained by the sensor is influenced by this parameter. However, this magnetic permeability is affected by the presence of electric current in the conductor, due to the effect of the magnetic field generated by the current. Indeed, although most of the current flows through the aluminum wires, a small part of it flows through the steel nucleus. As a consequence, the magnetic field generated in the interior of the conductor orients the magnetic dipoles and affects the effective permeability seen by the ECT sensor. As a result, the reader of an ECT sensor is modulated by the alternate current which flows through the conductor. This effect, if not compensated, restricts the use of ECT exclusively to de-energized lines.

b) The ECT technique also depends on the electrical conductivity of the conductors, which is to say, the signal obtained by the sensor is influenced by this parameter. As the electrical conductivity depends on the temperature, the reader of an ECT sensor will also be influenced by this parameter. This aspect is particularly important in energized lines, where the temperature of the conductor my reach more than 100° C.

c) The presence of aluminum wires reduces the sensitivity of the ECT technique by reducing the ratio of the area of steel to the area of solenoid (fill factor). As only the flow of the steel brings useful information to the ECT technique, the additional flow due to the increase in the diameter of the solenoid is added to the flow of the steel and reduces the sensitivity of the measurement. For example, if the ratio between the flow in the steel and the total flow of the solenoid is 0.8, it means that a variation of 10% in the flow of the steel will result in a variation of 8% in the flow of the solenoid. Whereas, if the ratio between the flow in the steel and the flow in the solenoid is reduced to 0.2, this means that the same variation of 10% in the flow of the steel will cause a variation of only 2% in the flow of the solenoid.

Objective of this Patent

This patent is intended to preserve the invention rights over a device for the inspection of energized electrical energy cable lines, which use ECT (Eddy Current Testing) to evaluate the remaining thickness of the zinc layer which covers the galvanized steel wires of the inspected cables. The original aspect of this invention consists of the implementation of a device for the inspection of energized electrical energy cable lines which use techniques which allow for the use of ECT in the evaluation of energized cables. For this purpose, techniques which compensate for the problems associated with the application of ECT in energized cables were developed, implemented and tested. The device using these techniques is described in this patent and contains its principal claims.

Technical, Commercial and Economic Advantages of the Invention

The main technical advantage of using ECT (Eddy Current Test) in relation to using WRT (Wire Rope Test) in ASCR cables of energized lines consists of the possibility of detecting the corrosive process while still in its initial stages. As the ECT technique makes it possible to determine the remaining thickness of the galvanization layers of the ASCR cables, the result of the inspection may indicate whether the cable still has reasonable protection against corrosion or if the corrosive process is already established. In commercial terms, the use of ECT in energized lines is an innovation which creates the possibility of a commercial advantage for a company which provides this service, as there is no equivalent on the market. As described previously, the existing inspection systems for conductors on the market, which work with energized lines, use the WRT technique.

The economic advantage for a concessionaire which uses ECT inspection in its lines derives from the replacement of the conductors which really need to be replaced. In comparison with the WRT technique, ECT inspection makes it possible to develop an inspection plan for lines based on the state of galvanization of the steel. In comparison with the conventional technique, which consists of the replacement of conductors based on time of service and visual inspection, ECT inspection prevents conductors in a good state from being replaced and compromised conductors from remaining in service. These advantages translate into a significant reduction in maintenance costs and in an increase in the continuity of supply of electrical energy. In other words, a predictive maintenance program for transmission lines based on the inspection of the state of their conductors allows the concessionaire to manage its transmission assets with greater efficiency and, as a result, maximize its economic results.

DETAILED DESCRIPTION OF THE INVENTION

The cable inspection device loaded onto a remotely-controlled robot, which is installed in the conductor of an energized electrical line. This robot communicates with a computer located at ground level through a radio beam, in such a way that the operator is able to supervise the data from the robot and control its movement. The data obtained by the ECT sensor are also transmitted to a computer, where they are shown on the screen and stored for subsequent analysis. Simply for illustrative purposes, FIG. 1 shows a photograph of the robot developed, which carries with it the ECT sensor which is the object of this patent application.

Below are described the techniques developed to allow the use of ECT in the inspection of energized lines. This techniques seek to:
  Compensate for the modulation of the magnetic permeability of the steel;
  Compensate for the effect of the temperature on electrical conductivity;
  Increase the sensitivity of the ECT reading.

Figure 2:
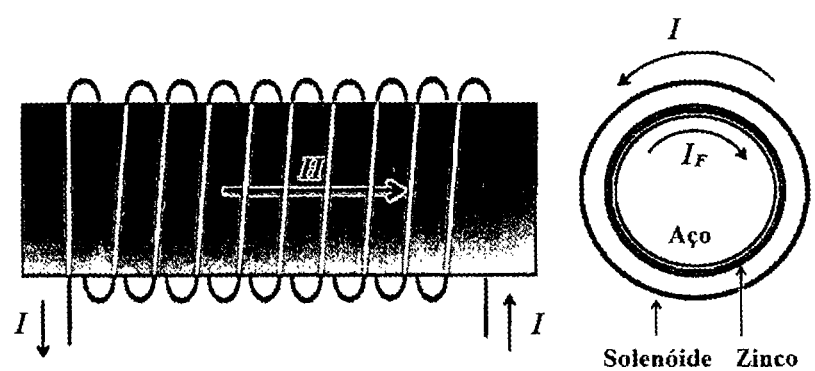
FIG. 2 is a simplified diagram of a system for inspection by ECT.

Technique for Compensating the Modulation of the Magnetic Permeability of the Steel FIG. 2 illustrates in a simplified manner the ECT technique, where a current I is applied to a solenoid which surrounds a conductor which will be inspected. This current generates a magnetic field H along the conductor, which induces eddy currents in the zinc layer which covers the steel. This induced current (IF in FIG. 2) tends to circulate in the opposite direction of the solenoid current, in such a manner as to cancel out the resulting magnetic flow. So the resulting magnetic flow is related to the thickness of the zinc layer and may be theoretically correlated with it [14].

Detection of the resulting magnetic flow may be effected by the same solenoid or by another solenoid surrounding the conductor, depending on the peculiarities of the circuit implemented. In both cases, the signal detected is digitalized and used to calculate the thickness of the zinc layer through specific theoretical formulations.

The current applied to the solenoid is alternate, with a frequency normally in the order of 40 kHz to 100 kHz. As such, the resulting magnetic flow and the tension induced by this in the solenoid are also alternate and at the same frequency as the current applied.

The application of an electrical current along the inspected conductor causes the magnetic domains of the steel to be partially oriented in an azimuthal direction (which is to say, in a circular direction, like the $I_F$). This orientation of the dipoles translates into an apparent reduction in the magnetic permeability of the steel. As the magnetic flow depends on the permeability, the signal captured by the solenoid proceeds to be modulated by the current of the conductor.

Figure 3:
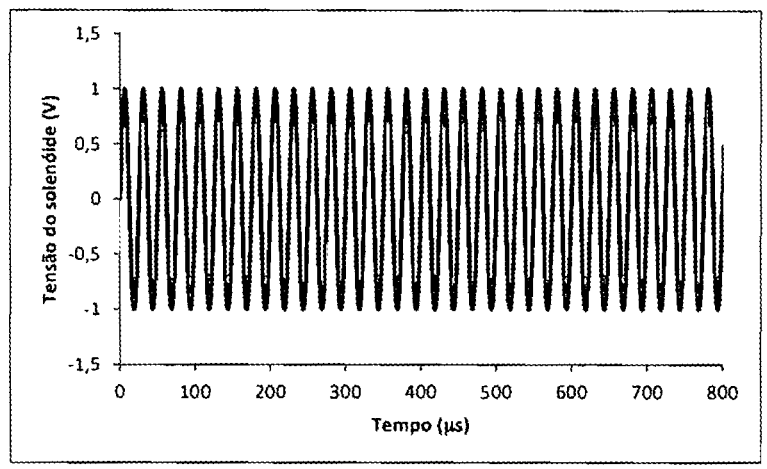
FIG. 3 is a diagram representing the solenoid signal when there is no current in the conductor.
Figure 4:
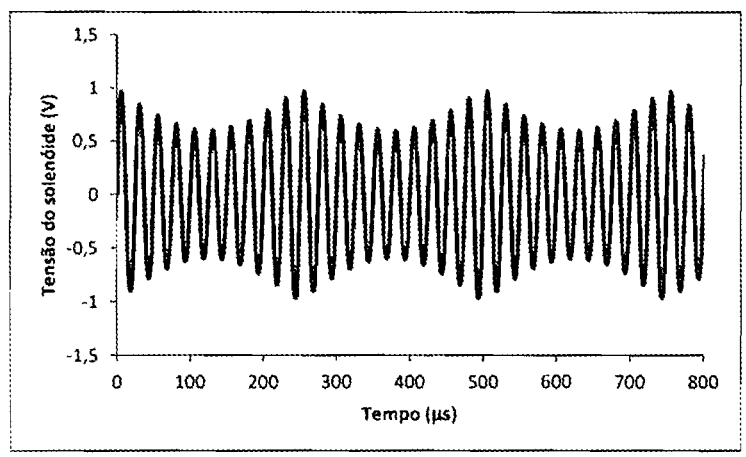
FIG. 4 is a diagram representing the solenoid signal when the conductor is conducting a 2 kHz current.

FIG. 3 shows the 40 kHz signal captured by a solenoid which surrounds a conductor which does not conduct electrical current, while FIG. 4 shows the signal captured by the same sensor when the conductor is conducting an alternate current of 2 kHz. It may be observed in FIG. 4 that the signal from the solenoid is modulated by the current of the conductor. In practice the current in the conductor has a frequency of 60 Hz, but 2 kHz for showing the effect of the modulation.

Figure 5:
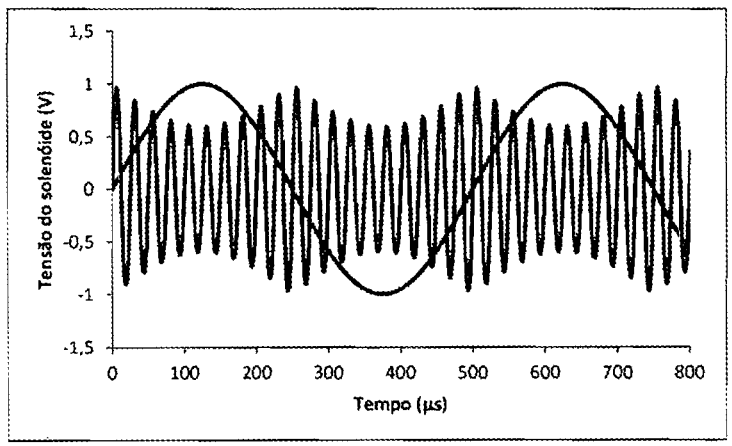
FIG. 5 is a diagram representing the solenoid signal (in the background) and the 2 kHz current (in the foreground).

FIG. 5 shows the modulating current over the modulated signal, where it may be observed that the modulated signal recovers its value without modulation when the current in the conductor reaches zero. As the frequency of the modulating signal is much lower than that of the measurement signal it is possible to perform an ECT measurement during the time interval when the current in the conductor is close to zero.

As such, with a view to rendering the measurement signal of the ECT sensor immune to the modulating effects of the current in the conductor, a technique was implemented in the measuring device which makes it possible to register the value measured during the time interval when the current in the conductor is close to zero.

Of the various possible techniques, a technique was implemented which performs measurements of the solenoid signal at short time intervals. For example, when the modulating wave has a frequency of 60 Hz, its period is 16.67 ms. Performing readings every 0.5 ms means that around 33 readings will be performed asynchronously over a cycle of 60 Hz, totaling 200 readings at the end of 0.1 seconds. These readings are digitally processed by the software installed (firmware) with a view to selecting the highest, which is to say, that which corresponds to moment when the current reaches zero (see FIG. 5). This value is then registered as a valid value and transmitted to the control computer, through the radio beam. As a result, it is possible to contain the problem of variation of the magnetic permeability of the steel with the current in the conductor.

There are other ways to register the ECT reading when the current reaches zero, which are different to that described above, but obvious to those involved in designs of electric/electronic circuits. For example, an auxiliary bobbin may be used to capture the magnetic field generated by the current in the conductor. The tension induced in this auxiliary bobbin will be dephased by 90° in relation to the current of the conductor, in such a manner that the moments when the current reaches zero correspond to the maximum and minimum moments of tension induced. Thus, monitoring of the tension induced may serve as a reference for determining the moment to carry out the recording of the ECT reading. In other words, the tension induced serves as a synchronization signal for ECT readings.

Technique for Compensating the Effects of Temperature on Electrical Conductivity As previously described, temperature affects the electrical conductivity of the metals which compose the cable (which is to say, steel, zinc and aluminum). For a de-energized line, this aspect is not critical, as the conductor will have a temperature much closer to the ambient temperature, its being sufficient to record this temperature for subsequent correction of the readings performed. However, the cable of an energized line operates at a very high temperature, which may exceed 100° C. In addition to this, the temperature of the conductor may vary along the inspected section, depending on environmental conditions (for example, wind variations) and the existence of structures which dissipate heat (such as vibration dampers). So, it is necessary to record the temperature of the conductor during the inspection.

The technique used to monitor the temperature of the conductor consists of inserting a temperature transducer into the head of the ECT sensor, so that this sensor monitors the temperature of the cable. The signal sent by the sensor is processed by an electronic circuit and transmitted to the ground computer, together with the other data read (which is to say, the position of the sensor and the ECT readings).

The information about the temperature is used in the computer program for analyzing the collected data, so that the conductivity of the materials involved is corrected for the temperature of the inspected cable.

Technique for Increasing the Sensitivity of the ECT Reader

As seen previously, the ECT reading of an ASCR cable has its sensitivity prejudiced because the area occupied by the steel within the solenoid is relatively small. This fact becomes particularly important if the same solenoid is used to inspect different cables. For example, the solenoid developed for this application has an internal diameter of 40 mm, which permits the inspection of cables up to a gauge of 1113.0 MCM (external diameter of 32 mm). In this case, the area of the nucleus of the cable is 39 mm$^2$, which corresponds to only 2.5% of the areas of the sensor. In other words, only the flow existing in 2.5% of the area of the solenoid carries useful information, while the flow of the remaining area (87.5%) enters the measuring system, but does not bring information.

Figure 6:
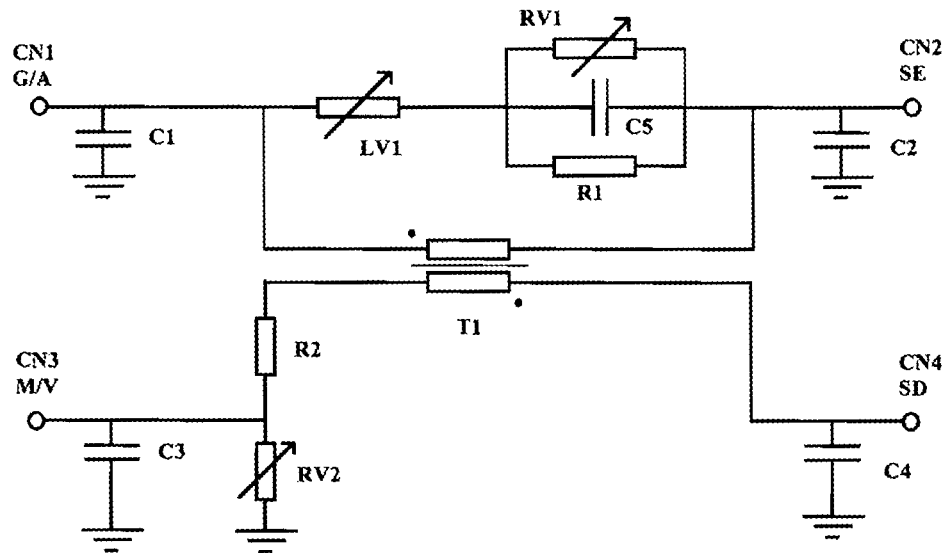
FIG. 6 represents a hybrid circuit used to increase the sensitivity of the ECT measuring.

To separate the useful flow from the useless flow, a specific hybrid circuit was developed for this application. The electrical diagram of the hybrid circuit is shown in FIG. 6. In this circuit, the current which comes from the generator (G/A) arrives at the connector CN1, passes through the variable inductor LV1 and through the parallel circuit formed by the variable resistor RV1, by the fixed resistor R1 and by the capacitor C5, before proceeding to the excitation solenoid (SE) through the connector CN2. The tension resulting from the passing of the current from the generator through the primary hybrid circuit is transferred to the secondary hybrid circuit through the transformer T1. This transformer also causes a phase inversion of the primary tension. As a result, the tension developed in the secondary [hybrid circuit?] of transformer T1 is subtracted from the tension which comes from the detection solenoid (SD) through the connector CN4 and is subsequently dampened by the voltage divider formed by the variable resistor RV2 and the fixed resistor R2. The resulting tension in the connector CN3 is then amplified, processed and digitalized.

For a given conductor, the parameters of the components of the hybrid circuit are adjusted so that the tension developed in the transformer T1 corresponds to the contribution of the useless flow to the tension of the detection solenoid. As a result, only the useful signal is supplied to the amplifier and the voltmeter (MN).

Implementation of the Techniques for Use of ECT in an Energized Line

Figure 7:
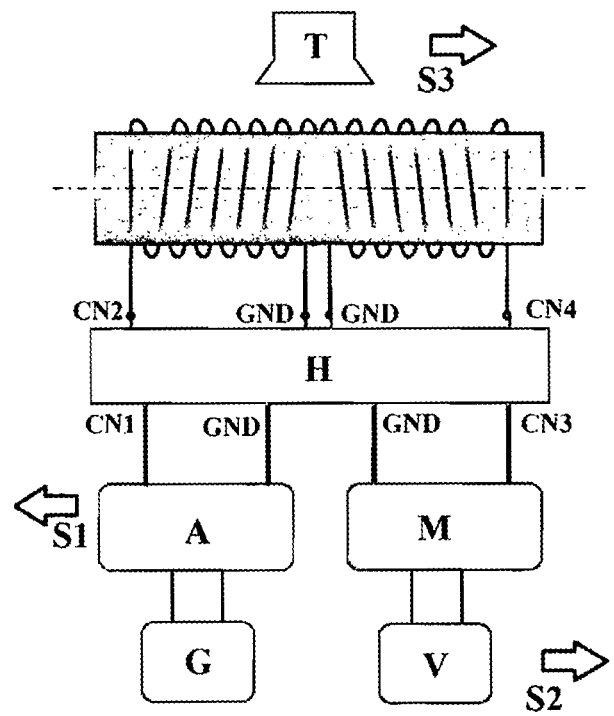
FIG. 7 represents a circuit for the use of ECT in the inspection of an energized conductor.

This section describes the incorporation of the techniques described previously into a circuit for carrying out measurements based on ECT (Eddy Current Testing) in ASCR cables of energized electric lines. The circuit is shown in FIG. 7 and its component blocks are described below:

G (Generator): Electronic circuit fed in a continuous current (12 V) which generates a sine wave with a minimum of harmonic distortion. There are various ways of implementing this signal-generating circuit, many of which are described in the technical literature. In this implementation a Wien bridge oscillator was used with thermal stabilization, however this implementation is not a limiting factor of the invention. In other words, other circuits may be used to generate a sine wave, without this representing a variant of this invention. The oscillation frequency of the generator was fixed at 45 kHz, through the adjustment of its parameters.

A (Ampere-meter): Electronic circuit used to measure the current which is applied to the excitation solenoid. There are also many ways of implementing this measurement, which can measure the current in a phased or scaled manner. In this implementation it was opted to use a measurement of a scaled value based on a quasi peak detector, although this implementation is not a limiting factor of this invention. This detector obtains a tension signal proportional to the value of the peak of the current, using a rectification and integration circuit. The signal measured (S1) is submitted to the port (A/D) of the micro-controller (analog/digital converter) and digitalized.

V (Voltmeter): Electronic circuit which is used to measure the tension which comes from the detection solenoid (SD), after passing through the Hybrid Circuit and the Amplifier. There are also different ways of implementing this measurement, which can measure the tension in a phased or scaled manner. In this implementation it was decided to use a measurement of scaled value based on a quasi peak detector, although this implementation is not a limiting factor of this invention. This detector obtains a tension signal proportionate to the peak value of the tension at the amplifier outlet, using a rectification and integration circuit. The signal measured (S1) is submitted to the port (A/D) of the micro-controller (analog/digital converter) and digitalized.

M (Amplifier): Electronic circuit which is used to amplify the signal from the detection solenoid, after passing though the Hybrid Circuit, so that it has an amplitude compatible with the voltmeter. In this implementation, an operational amplifier was used for this function, although there are other options for this Amplifier, without its representing a limitation of this invention.

H (Hybrid Circuit): A passive circuit with four terminals, responsible for extracting from the tension captured by the detection solenoid that portion of tension which carries information about the ASCR steel nucleus. The Hybrid Circuit was previously described and constitutes an integral part of this invention, as it enables the ECT technique used to have sufficient sensitivity to inspect an ASCR cable.

T (Thermometer): Temperature transducer and associated electronic circuit, which seek to provide a measurement of the temperature of the conductor. There are different ways of implementing this Thermometer, depending on the transducer technology used, for example, infrared light, semi-conductor junction tension, thermocouple, etc. In this invention, semi-conductor junction tension was used, although this does not represent a limitation of this invention, which is to say, other technologies may be used to measure the temperature of the conductor without their representing a variation on this invention. The S3 signal obtained is submitted to the A/D converter of the micro-controller and digitalized.

The temperature value obtained from the conductor (based on S3) is used to obtain the conductivity of the zinc and aluminum, based in their conductivity at a reference temperature (for example, 20° C.). For this purpose, the following formula is used:

$$\sigma(T) = \sigma(T_0)[1 + k(T - T_0)]$$

where T is the temperature of the conductor, $T_o$ is the reference temperature, a is the conductivity of the metal considered and k is the variation coefficient of the conductivity with the temperature.

The value of the tension of the sensory bobbin (S1) is divided by the value of the current (S2), obtaining the impedance of the solenoid used. Dividing this value by the reading of the solenoid without the semi-conductor (which is to say, empty), the normalized impedance ($Z_N$) of the solenoid is obtained. This value and the conductivity of the metals are used in a formula (for example, [14]) to calculate the thickness of the zinc layer.

As previously described, the measurements of the S1 and S2 signals are performed at brief intervals, in comparison to the time periods of the industrial frequency current (for example, 60 Hz). For example, in this implementation, the S1 and S2 readings (and, as a consequence, the impedance of the solenoid) are realized every 0.5 ms, so that 200 readings are carried out asynchronously in 0.1 seconds. These readings are processed digitally by the software installed (firmware) with a view to selecting the highest, which is to say, that which corresponds to the current's reaching zero (see FIG. 5). This value is then recorded as a valid value and made available for transmission to the control computer, via the radio beam. As a result, it is possible to contain the problem of variation of the magnetic permeability of the steel with the current in the conductor.

In summary, the application of the ECT technique in the inspection of ASCR conductors in energized lines requires that:

The reading of the impedance of the solenoid is performed while the current is passing from 60 Hz to zero (see previous description);

The conductivity values of the metals are corrected by the temperature of the conductor, which should be measured during the inspection (see previous description);

The sensitivity of the reading is increased, with a view to compensating the useless flow captured by the solenoid (see previous description).

These three techniques were successfully implemented in the device developed and represent the principal claims of this invention.

REFERENCES

[1] C. F. Barbosa, F. E. Nallin, P. C. Gisolfi and C. Aoki, "Sensor e sistema para detecçao da corrosão em camada de zinco sobre aço," ("Sensor and system for detecting corrosion of zinc on steel"), Invention Privilege, Registro PI 0705769-5 A2, filing date: Jun. 8, 2007.
[2] L. B. Geller, D. Pophenroth, J. E. Udd, and D. Hutchinson, "Evaluation of electromagnetic rope testers: Joint Canadian-US work," Materials Evaluation, vol. 50, no. 1, pp. 56-63, 1992.
[3] U.S. Pat. No. 4,427,940, "Electromagnetic inspecting apparatus for magnetizable wire rope", Hitachi Elevator Eng. and Service Ltd., 24 Jan. 1984.
[4] U.S. Pat. No. 4,727,321, "Method and device for magnetic and ultrasonic testing of ferromagnetic objects", Nukem Gmbh, 23 Feb. 1988.
[5] U.S. Pat. No. 4,763,070, "Method and apparatus to compensate for lateral changes of a ferromagnetic body during magnetic testing", Nukem Gmbh, 20/Set./1985.
[6] U.S. Pat. No. 4,827,215, "Method and apparatus for magnetic saturation testing a wire rope for defects", Crucible SA, 19 Mar. 1987.
[7] U.S. Pat. No. 5,321,356, "Magnetic inspection device for elongated objects and inspection method", Ndt Tech. Inc., 26 May 1992.
[8] U.S. Pat. No. USRE40166 E, "Magnetic non-destructive method and apparatus for measurement of cross sectional area and detection of local flaws in elongated ferrous objects in response to longitudinally spaced sensors in an inter-pole area", Intron Plus Ltd., 25 Mar. 2008.
[9] Kinectrics, "LineVue: Advanced non-destructive technology for accurate conductor assessment", Kinectrics brochure, 27 Set. 2010.
[10] A. V. Pinto Jr., M. Z. Sebrao, C. R. S. C. Lourengo, I. S. Almeida, J. Saad, and P. M. Lourengo, "Remote detection of internal corrosion in conductor cables of power transmission lines," 1st Int. Conf. on Applied Robotics for the Power Industry, Montreal, Canada, Out. 2010.
[11] C. R. S. C. Lourengo et al., "Robo para inspegao de cabos condutores", ("Robot for inspecting conductor cables") Invention privilege, Registration no. PI 0905866-4 A2, filing date: Dec. 16, 2009.
[12] Patent EP 1000349A1, "Apparatus and method of detecting loss of cross-sectional area of magnetic metallic strength members used in conductors such as aluminum conductor steel reinforced (acsr) conductors", J. Brooker, 17 May 2000.
[13] F. Forster and Stambke, "Theoretische and experimentelle Grundlagen der zerstorungfreien WerkstoffprOfung mit Wirbelstromverfahren", Zeits. Metallkde., Bd. 45, Heft. 4, pp. 166-179, 1954. Apud Wait [14].
[14] J. R. Wait and R. L. Gardner, "Electromagnetic non-destructive testing of cylindrically layered conductors," IEEE Trans. on Instrum. Meas., vol. 28, n. 2, pp. 159161, June 1979.
[15] J. Sutton and K. G. Lewis, "The detection of internal corrosion in steel-reinforced aluminum overhead transmission lines," Proc. of UK Corrosion '86, vol. 1, pp. 345-359, Birmingham, UK, 1986.
[16] P. H. Schwabe and D. Pike, "The measurement of corrosion in overhead power line," Anti-corrosion, July, 1988.
[17] Y. Kojima, J. Fukuda, T. Kumeda, J. Iinuma, and M. Endo, "Corrosion detector robot for overhead transmission line," Fujikura Technical Review, n. 21, pp. 74-83, 1992.
[18] D. G. Havard, G. Bellamy, P. G. Buchan, H. A. Ewing, D. J. Horrocks, S. G. Krisnasamy, J. Motlis, and K. S. Yoshiki-Gravelsins, "Aged ACSR conductors, Part I: Test procedures for conductors and line items," IEEE Trans. on Power Delivery, vol. 7, n. 2, pp. 581-587, April 1992.
[19] National Grid, Innovation Funding Incentive (IFI) Annual Report 2012/13: Electricity Transmission—Detection and measurement of ACSR corrosion," pp. 118-119.

The invention claimed is:
1. Device for inspecting aluminum cables with a steel core (ASCRs), installed in energized electrical energy lines, characterized by the fact that it encompasses a circuit for measuring based on ECT (Eddy Current Testing) in ASCR cables of energized electrical lines, consisting of:

Generator (G) implemented using a sinusoidal oscillator operating through a Wien bridge with thermal stabilization or a similar technique;

Ampere-meter (A) consisting of a rectification and integration circuit, or a similar technique, used to measure the current which is applied in an excitation solenoid;

Voltmeter (V) consisting of a rectification and integration circuit, or a similar technique, used to measure the tension which comes from a detection solenoid (SD), after passing through a Hybrid Circuit and an Amplifier;

the Amplifier (M) consisting of an electronic circuit used to amplify the signal from the detection solenoid, after passing through the Hybrid Circuit;

the Hybrid Circuit (H) consisting of a passive circuit of four terminals, which combines the signal applied to the excitation solenoid with the signal received from the detection solenoid, with a view to increasing the sensitivity of the measurement;

Thermometer (T) consisting of a temperature transducer and associated electronic circuit, intended to provide a measurement of the temperature of a conductor.

2. Device, in accordance with claim 1, characterized by the fact that the readings of the tension of the detection solenoid and the current of the excitation solenoid are taken as the current in the inspected conductor reaches zero.

3. Device, in accordance with claim 1, characterized by the fact that the electrical parameters of the conductor are corrected for the temperature measured by the Thermometer (T).

4. Device, in accordance with claim 1, characterized by the fact that the signal from the detection solenoid is filtered by the Hybrid Circuit (H), with a view to extracting the portion of tension associated with the nucleus of the conductor inspected and, as such, to increasing the sensitivity of the measurement.

5. Method for inspecting aluminum cables with a steel core (ASCRs), installed in energized electrical energy lines, characterized by the fact that the readings of the tension of a detection solenoid and the current of an excitation solenoid are taken as the current in an inspected conductor reaches zero;

The electrical parameters of the inspected conductor are corrected for its temperature, which should be measured during its inspection;

The signal from the detection solenoid is filtered through a Hybrid Circuit (H), with a view to extracting the portion of tension associated with the nucleus of the inspected conductor and, as such, increasing the sensitivity of the measurement.

* * * * *